United States Patent [19]

Smith

[11] Patent Number: 4,601,716
[45] Date of Patent: Jul. 22, 1986

[54] DISPOSABLE SANITARY SHEATH FOR MALES

[76] Inventor: Lonnie W. Smith, 1429 Palo Loma, Orange, Calif. 92669

[21] Appl. No.: 722,843

[22] Filed: Apr. 11, 1985

[51] Int. Cl.$^4$ .............................................. A61F 5/44
[52] U.S. Cl. .................................... 604/349; 604/351; 604/353
[58] Field of Search ................... 128/760, 767, 132 R, 128/DIG. 15; 604/317, 346–354, 359, 360, 365, 378, 381; 4/144.1–144.4

[56] References Cited

U.S. PATENT DOCUMENTS

| | | | |
|---|---|---|---|
| 2,873,740 | 2/1959 | Wainwright | 604/349 |
| 3,585,998 | 6/1971 | Hayford | 604/360 |
| 3,586,001 | 6/1971 | Sanderson | 128/DIG. 15 |
| 3,648,700 | 3/1972 | Warner | 604/349 |
| 3,901,240 | 8/1975 | Hoey | 604/359 |

FOREIGN PATENT DOCUMENTS

| | | | |
|---|---|---|---|
| 779920 | 4/1935 | France | 604/349 |
| 2016929 | 9/1979 | United Kingdom | |

*Primary Examiner*—J. L. Kruter
*Attorney, Agent, or Firm*—Plante Strauss & Vanderburgh

[57] ABSTRACT

There is disclosed a sanitary disposable sheath intended for wearing on the penis of males which is formed with a moisture absorbent pad to absorb excretions and urine. The sheath is intended for use by normal, healthy males and not as a prosthetic device, and a method of use is also disclosed and claimed. Preferably, the sheath is formed as a laminate of an outer moisture resistant sheath and an inner, coextensive, moisture permeable liner, with an intermediate moisture absorbent pad. The sheath is provided with either an elastic band closure about its neck, or Velcro type fabric attachment bands to retain it distally on a penis.

20 Claims, 4 Drawing Figures

U.S. Patent   Jul. 22, 1986   4,601,716
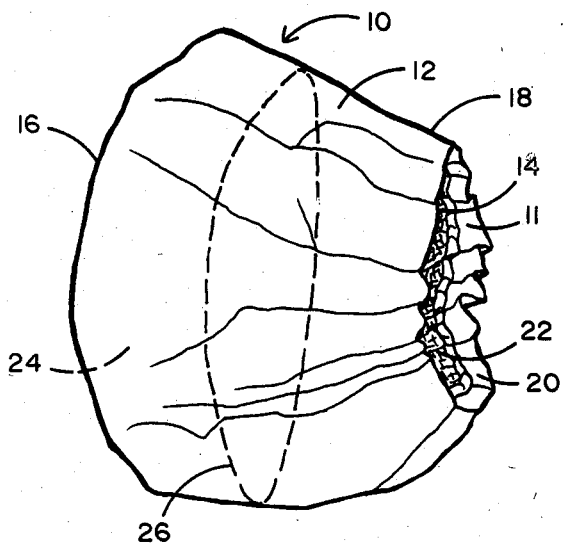
FIG. 1
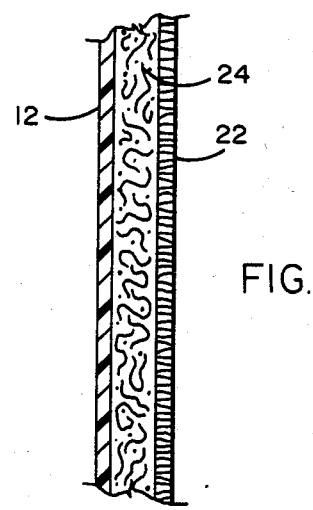
FIG. 2
FIG. 3
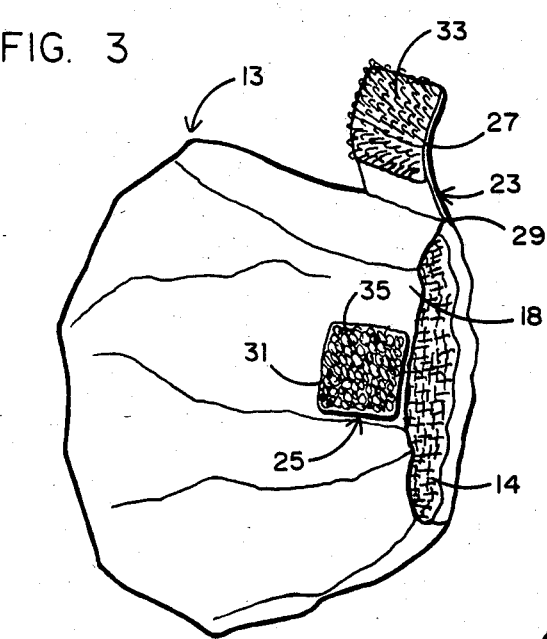
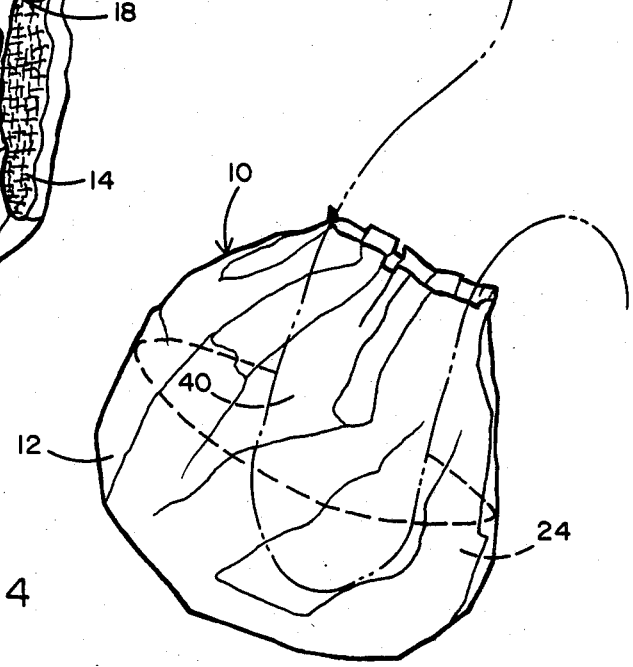
FIG. 4

DISPOSABLE SANITARY SHEATH FOR MALES

BACKGROUND OF THE INVENTION

1. Field Of The Invention

This invention relates to a sanitary disposable pad, and in particular to such a pad for use by males.

2. Brief Statement Of The Prior Art

Disposable sanitary napkins and tampons are commonly used by adult females for absorbing uterine flow and, of course, disposable diapers are commonly used on infants. There have also been various absorbent prosthetic devices intended to arrest hemmorages or abosrb secretions. Adult males, however, have not previously worn sanitary pads or devices, and none has previously been successfully provided for such use. The sphincter of the male urinary canal often functions imperfectly, leading to momentary post urination dripping or excretion, presenting a hygienic problem, and a need, therefore, exists for a disposable, sanitary pad for use by healthy males.

BRIEF DESCRIPTION OF THE INVENTION

This invention comprises a disposable sanitary sheath, and a method of its use by males. The sanitary sheath has an outer covering having a single opening and an interior cavity; with a neck having either an elastic closure band encircling the large opening with an inside liner coextensive with its interior cavity that is formed of a moisture permeable sheet material; and an intermediate pad between said outer sheath and said inside liner, coextensive with at least the central area thereof, and formed of a moisture absorbent material. Preferably the sheath has a generally bag shape and the elastic band should provide sufficient tension to retain said sheath distally about a penis. Alternatively, the sheath can have a cooperating pair of Velcro type fabric attachment tabs about its neck which are spaced apart a sufficient distance to permit retention of the sheath distally on a penis when the fabric attachment tabs are engaged.

BRIEF DESCRIPTION OF THE DRAWINGS

The invention will be described with reference to the FIGURES, of which:

FIG. 1 is a perspective view of one embodiment of the sheath of the invention;

FIG. 2 is a sectional view through the wall of the sheath of FIG. 1;

FIG. 3 is a perspective view of another embodiment of the sheath of the invention; and FIG. 4 illustrates the proper wearing of the sheath.

DESCRIPTION OF PREFERRED EMBODIMENTS

Referring now to FIG. 1, the invention is a sheath 10 formed of an outer sheathing 12 which is formed of a moisture impermeable material, preferably formed of a woven fabric, of a natural fiber such as cotton, or of a synthetic fabric such as polyester, rayon, Nylon, etc. Alternatively, the material could be non-woven, e.g. a plastic film of a suitable resin, e.g., polyethylene, polyethylidene chloride, etc. When formed of a woven fiber, preferably, the material is coated or impregnated with water resistant coating which imparts moisture impermeability to the fabric.

The sheath 10 is formed with a single large opening 12 and an interior cavity 14. Preferably, the sheath 10 is formed into the bag-like shape without seams or corners with a rounded bulbous end 16, and a neck 18 about the large opening 12. An elastic band, not shown is secured about the neck 18, and for this purpose, the edge of the material can be folded inwardly, and secured in a continuous seam 20 about the neck 18, and the elastic band can be placed in seam 20. The inside seam can be secured by suitable means, e.g., by a continuous fiber stitch about the neck, or by a narrow band of fabric cement. The elastic band should provide sufficient tension about the neck to retain the sheath distally about a penis, preferably it should constrict the opening 12 to approximately $\frac{1}{4}$ to $\frac{1}{2}$ its diameter, when unstretched, as shown in FIG. 1.

The interior cavity 14 is lined entirely with an inside liner 22 which is coextensive with the this cavity 14. The inside liner 22 is moisture permeable, and can be formed of a woven fabric of a natural fiber such as cotton. Alternatively, the fabric is formed of a fiber having no water absorbency, such as polyester, Nylon, rayon, etc. The inside liner 22 is of the same shape and dimensions as the outer sheathing 12 and is secured thereto, at least about the inside surface of the neck 18. This can be achieved by extending the edge of the inside liner 22 into the seam 20.

The sanitary sheath 10 also includes a pad 24 of moisture absorbent material which is coextensive with at least the central area of the sheath 10, shown by phantom line 26. Preferably, the pad 24 is formed of a moisture absorbent material such as cotton fibers or linters which can be woven into a fabric, or can be loosely consolidated in random order and bonded together into a padding with suitable means, such as stitching or cementing.

Referring now to FIG. 2, the construction of the sheath 10 will be described. As previously mentioned the sheath is a laminate of an outer sheathing 12 of film or fabric which is moisture resistant, an inner liner also of film or fabric which is moisture permeable, and an intermediate pad 24 which is formed of consolidated moisture absorbent fibers. The pad 24 is of substantially greater thickness than the outer sheathing 12 and inside liner 22, having a thickness from about $\frac{1}{8}$ to about $\frac{1}{2}$, preferably from about $\frac{1}{8}$ to about $\frac{1}{4}$, inch.

Referring now to FIG. 3, an alternative construction is illustrated. The sheath 11 has the same bulbous shape as that shown in FIG. 1, however, the elastic band is replaced with an alternative attachment which comprises a pair of mating and cooperative fabric attachment tabs 23 and 25. The tabs 23 and 25 have a woven fabric backing 27 which is secured to the outer sheathing 12 at spaced apart positions, 29 and 31, along the neck 18. The distance between positions 29 and 31 should be about $\frac{3}{4}$ to about 1.5 inches, preferably about $\frac{3}{4}$ to about $1\frac{3}{8}$ inches, so that the large opening 14 can be constricted to 50 to 75 percent of its diameter when fabric tabs 23 and 25 are secured. Each tab is distally provided with a short length 33 and 35 of looped fabric. The length 33 has 33 has on its undersurface, a plurality of small fiber hooks, while the cooperating length 35 has a plurality of small fiber loops on its outer surface which are capable of engaging and securing the fiber hooks of length 33. Fabric of this construction is conventionally available under the mark Velcro. Tabs 23 and 25 can otherwise be identical, however, it is preferred to secure tab 25 to the outer sheathing along its entire undersurface. Preferably, at least one of the tabs 23 and 25 is of sufficient length to provide a variable degree of closure of the neck of the sanitary sheath 10, throughout the aforementioned range.

The invention also comprises a method of use of the sheathing 10. A healthy male, i.e., one with no medical complications or infections in his urinary track can apply the sanitary sheath 10 about the end 40 of his penis, shown in phantom lines in FIG. 4, and can routinely wear the sanitary sheath 10 as a hygienic item, removing it prior to urination, and then returning it, or replacing it with a fresh sanitary sheath immediately upon completion of urination, so that the sheath will trap or absorb any post urination excretion. The sheath 10 distally fits loosely over the penis and the elastic band gathers the sheath material in folds, as shown in FIG. 4. Since the inside liner is moisture permeable, but is not absorbent, it will remain dry, while the moisture absorbent pad 24 will be effective to absorb all unintentional daily excretions, and can be disposed of and replaced with a fresh sheath 10 daily. The clothing is protected since the outer sheathing 12 is impermeable to moisture, and all excretions are thus trapped within the sanitary sheath 10.

For additional sanitary protection, the sanitary sheath 10 can be coated or impregnated with a suitable microcide, e.g., a fungicide such as those commonly used for topical fungus treatment, e.g., Tolnaftate solution at an effective concentration, e.g., from 1 to about 5 weight percent. Preferably the fungicide is impregnated at an effective dosage, e.g., from about 0.5 to about 5 weight percent, onto the fibers which are consolidated into the water absorbent pad 24, either before or after their consolidation and formation as a unitary pad. The actual concentration will vary, of course, with the effective concentrations of the particular fungicide which is used.

Other materials can also be impregnated or coated onto the sanitary sheath 10, such as deodorants or fragrances which are commonly used for body deodorants or perfumes. As with the microcide, the effective amounts of these materials will also vary with the particular material selected. Preferably these materials, also, are impregnated into the moisture absorbent pad 24.

If desired, the additive to the pad 24, either or both a fragrance and a fungicide, can be moisture sensitive, i.e., bound to the pad 24 and released only when the pad is moistened. This can be achieved, e.g., by adsorbing the additive such as a fragrance onto a solid carrier such as silica gel, alumino-silicates such as molecular sieves, etc., so that moisture which contacts the carrier will be effective in releasing the adsorbed fragrance. The solid carrier can then be physically incorporated into pad 24, or can be bonded to the fibers of pad 24 with a suitable adhesive. As an additional means of providing water release, the solid carrier, after adsorption of the agent, either or both the fragrance and fungicide, can be coated with a water soluble coating, e.g., polyvinyl acetate, such as that commercially available as Elevanol from E. I. DuPont de Nemours & Co., 1007 Market Street, Wilmington, Del., to seal the agent in the carrier, and the carrier can then be incorporated in the intermediate pad 24. In another embodiment, the agent such as the fragrance or fungicide can be dispersed or dissolved in a polyvinyl alcohol and the resultant liquid can be coated on some of the fibers used in the intermediate pad 24 prior to their loose consolidation. In either embodiment, the agent will be released when moisture contacts the carrier, which is the aforementioned adsorbent, or fibers, and dissolves the polyvinylalcohol coating.

The disposable sheath has sufficient diameter and length to be loosely received, distally about a penis. For this purpose, it can be supplied in several sizes with a unconstricted diameter ranging generally from about 1 to about 2 inches, and a length ranging from about 1.5 to about 3 inches.

The invention has been described with reference to the illustrated and presently preferred embodiment. It is not intended that the invention be unduly limited by this illustration of the presently preferred embodiment. Instead, it is intended that the invention be defined by the means and steps, and their obvious equivalents, set forth in the following claims.

What is claimed is:
1. A disposable sanitary sheath, which comprises:
   (a) an outer sheath having a single opening and an interior cavity;
   (b) a neck with an elastic enclosure band encircling said single, large opening;
   (c) an inside liner within said sheath, coextensive with said interior cavity, and formed of a moisture permeable sheet material;
   (d) an intermediate pad between said outer sheath and said inside liner, coextensive with at least the central area thereof, and formed of a moisture absorbent material; and
   (e) a fungicide adsorbed onto a solid water sensitive solid carrier selected from the group consisting of silica gel and aluminosilicates which are incorporated into said intermediate pad;
said sheath having a generally bag shape with a diameter from 1 to about 2 inches and a length from 1.5 to 3 inches, sufficient to be loosely received distally over a penis, with said elastic band gathering its opening to its unrestricted diameter and providing sufficient tension to retain said sheath distally about a penis.

2. The disposable sanitary sheath of claim 1 formed with a rounded, bulbous shape, free of seams and corners.

3. The disposable sanitary sheath of claim 1 wherein said inside liner is formed of moisture permeable fabric.

4. The disposable sanitary sheath of claim 1 wherein said intermediate pad is formed of cotton.

5. The disposable sanitary sheath of claim 1 wherein said outer sheath is formed of fabric impregnated with a moisture resistant coating.

6. The disposable sanitary sheath of claim 1 wherein said closure band includes a pair of tabs of cooperating hook and loop fabric fasteners spaced about the outside of said neck.

7. A disposable sanitary sheath, which comprises:
   (a) an outer sheath having a single opening and an interior cavity;
   (b) a neck with an elastic enclosure band encircling said single, large opening;
   (c) an inside liner within said sheath, coextensive with said interior cavity, and formed of a moisture permeable sheet material;
   (d) an intermediate pad between said outer sheath and said inside liner, coextensive with at least the central area thereof, and formed of a moisture absorbent material; and
   (e) a perfume adsorbed onto a water sensitive carrier selected from the class consisting of silica gel and aluminosilicates which are incorporated into said intermediate pad, and which are effective to release said perfume when contacted with moisture;

said sheath having a generally bag shape with a diameter from 1 to about 2 inches and a length from 1.5 to 3 inches, sufficient to be loosely received distally over a penis, with said elastic band gathering its opening to its unrestricted diameter and providing sufficient tension to retain said sheath distally about a penis.

8. A disposable sanitary sheath, which comprises:
   (a) an outer sheath having a single opening and an interior cavity;
   (b) a neck with an elastic enclosure band encircling said single, large opening;
   (c) an inside liner within said sheath, coextensive with said interior cavity, and formed of a moisture permeable sheet material;
   (d) an intermediate pad between said outer sheath and said inside liner, coextensive with at least the central area thereof, and formed of a moisture absorbent material; and
   (e) a perfume bonded to said intermediate pad with a water soluble coating which is effective to release said perfume when contacted with moisture;

said sheath having a generally bag shape with a diameter from 1 to about 2 inches and a length from 1.5 to 3 inches, sufficient to be loosely received distally over a penis, with said elastic band gathering its opening to its unrestricted diameter and providing sufficient tension to retain said sheath distally about a penis.

9. The disposable sanitary sheath of claim 8 formed with a rounded, bulbous shape, free of seams and corners.

10. The disposable sanitary sheath of claim 7 formed with a rounded, bulbous shape, free of seams and corners.

11. The disposable sanitary sheath of claim 7 wherein said inner liner is formed of moisture permeable fabric.

12. The disposable sanitary sheath of claim 7 wherein said outer sheath is formed of fabric impregnated with a moisture resistant coating.

13. The disposable sanitary sheath of claim 7 wherein said closure band includes a pair of tabs of cooperating hook and loop fabric fasteners spaced about the outside of said neck.

14. The disposable sanitary sheath of claim 8 wherein said inner liner is formed of moisture permeable fabric.

15. The disposable sanitary sheath of claim 8 wherein said outer sheath is formed of fabric impregnated with a moisture resistant coating.

16. The disposable sanitary sheath of claim 8 wherein said closure band includes a pair of tabs of cooperating hook and loop fabric fasteners spaced about the outside of said neck.

17. A disposable sanitary sheath, which comprises:
   (a) an outer sheath having a single opening and an interior cavity;
   (b) a neck with an elastic enclosure band encircling said single, large opening;
   (c) an inside liner within said sheath, coextensive with said interior cavity, and formed of a moisture permeable sheet material;
   (d) an intermediate pad between said outer sheath and said inside liner, coextensive with at least the central area thereof, and formed of a moisture absorbent material; and
   (e) a fungicide bonded onto said intermediate pad with a water soluble coating effective to release said fungicide when contacted with moisture;

said sheath having a generally bag shape with a diameter from 1 to about 2 inches and a length from 1.5 to 3 inches, sufficient to be loosely received distally over a penis, with said elastic band gathering its opening to its unrestricted diameter and providing sufficient tension to retain said sheath distally about a penis.

18. The disposable sanitary sheath of claim 17 formed with a rounded, bulbous shape, free of seams and corners.

19. The disposable sanitary sheath of claim 17 wherein said inner liner is formed of moisture permeable fabric.

20. The disposable sanitary sheath of claim 17 wherein said outer sheath is formed of fabric impregnated with a moisture resistant coating.

* * * * *